(12) United States Patent
Spencer

(10) Patent No.: US 7,306,810 B1
(45) Date of Patent: Dec. 11, 2007

(54) SKIN CREAM

(75) Inventor: David M. Spencer, Winston-Salem, NC (US)

(73) Assignee: Piedmont Cosmeceuticals, Inc., Winston-Salem, NC (US)

( * ) Notice: Subject to any disclaimer, the term of this patent is extended or adjusted under 35 U.S.C. 154(b) by 87 days.

(21) Appl. No.: 10/303,493

(22) Filed: Nov. 25, 2002

(51) Int. Cl.
 *A61K 8/27* (2006.01)
 *A61K 8/36* (2006.01)
(52) U.S. Cl. .................. 424/401; 514/557; 514/844
(58) Field of Classification Search ............. 424/401, 424/59; 514/448, 557
 See application file for complete search history.

(56) References Cited

U.S. PATENT DOCUMENTS

| | | | |
|---|---|---|---|
| 4,007,266 A | 2/1977 | Choay | |
| 4,087,555 A | 5/1978 | Barnett et al. | |
| 4,268,526 A | 5/1981 | Vargas et al. | |
| 4,297,374 A | 10/1981 | Wess | |
| 4,362,747 A | 12/1982 | Coursen | |
| 4,760,096 A | 7/1988 | Sakai et al. | |
| 5,254,331 A | 10/1993 | Mausner | |
| 5,322,685 A | 6/1994 | Nakagawa et al. | |
| 5,362,488 A | 11/1994 | Sibley et al. | |
| 5,376,361 A | 12/1994 | Perricone | |
| 5,391,373 A | 2/1995 | Mausner | |
| 5,409,693 A | 4/1995 | Perriconne | |
| 5,545,398 A | 8/1996 | Perricone | |
| 5,554,647 A | 9/1996 | Perricone | |
| 5,574,063 A | 11/1996 | Perricone | |
| 5,643,586 A | 7/1997 | Perricone | |
| 5,658,580 A | 8/1997 | Mausner | |
| 5,709,868 A | 1/1998 | Perricone | |
| 5,817,621 A | 10/1998 | Goudzenko et al. | |
| 5,922,331 A | 7/1999 | Mausner | |
| 5,958,397 A | 9/1999 | Smerbeck et al. | |
| 5,965,618 A | 10/1999 | Perricone | |
| 6,015,548 A * | 1/2000 | Siddiqui et al. | ............ 424/59 |
| 6,146,650 A | 11/2000 | Redlinger | |
| 6,162,419 A * | 12/2000 | Perricone et al. | ............ 424/59 |
| 6,191,121 B1 | 2/2001 | Perricone | |
| 6,281,236 B1 | 8/2001 | Farber | |
| 6,296,861 B1 | 10/2001 | Perricone | |
| 6,319,942 B1 | 11/2001 | Perricone | |
| 6,365,623 B1 * | 4/2002 | Perricone | ............ 514/448 |
| 6,544,531 B1 * | 4/2003 | Cole et al. | ............ 424/401 |

OTHER PUBLICATIONS

Perricone, N., *The Wrinkle Cure*, Warner Books, New York, NY, 2000, entire book.

* cited by examiner

*Primary Examiner*—Sreeni Padmanabhan
*Assistant Examiner*—Gina C. Yu
(74) *Attorney, Agent, or Firm*—Kilpatrick Stockton LLP

(57) ABSTRACT

The present invention provides a skin cream which can be used by most individuals on a daily basis to improve the quality of skin tone. The skin cream of the present invention comprises at least one anti-oxidant, an anti-inflammatory agent, an exfoliant, and an agent to protect against UV irradiation. In addition, the skin cream of the present invention may comprise oils, creams, and/or other compounds to promote adsorption of the active ingredients and to increase vibrancy of the skin tone. For example, in an embodiment, the skin cream of the present invention comprises: (a) dimethylaminoethanol (DMAE), (b) α-lipoic acid, (c) lactic acid, (d) retinol, (e) zinc or titanium oxide, and (f) vitamin C, wherein components (a), (b), (c), (d), (e) and (f) are in amounts such that application of the cream to an individual increases the thickness of collagen bundles in the individual's skin.

19 Claims, No Drawings

SKIN CREAM

FIELD OF THE INVENTION

The present invention relates to skin creams. More particularly, the present invention provides a cream which when applied to the skin of an individual, provides increased firmness and reduced wrinkling of the skin.

BACKGROUND

Skin comprises three layers: a top or outer layer (epidermis); a middle layer (dermis); and an underlying fat layer. The epidermis includes the stratum corneum as the upper (surface) layer, which is a protective layer of dead skin cells. The lower layers of the epidermis are comprised of basal cells, which produce new skin. The dermis, which lies under the epidermis and makes up about 90% of the skin, includes nerve cells, receptors, sweat glands, sebaceous glands, blood vessels and hair follicles. The dermis also contains a dense meshwork of collagen and elastin which provides skin with strength and elasticity. Underneath the dermis is a protective fat layer that insulates the body and helps to keep the skin smooth.

It is known that application of certain natural products may be associated with reduced aging of the skin. For example, U.S. Pat. No. 6,146,650 uses liposomes to deliver collagen, avocado oil, aloe and vital nutrients such as vitamins A, C, D and E to the skin. Also, U.S. Pat. No. 6,281,236 describes compositions containing allantoin and an emulsifier for the treatment of skin.

Certain skin treatments target damaged tissue. Thus, U.S. Pat. No. 6,319,942, describes the use of alkanoamines such as dimethylaminoethanol (DMAE) for the treatment of scars; U.S. Pat. No. 6,296,861, describes the use of conjugated linoleic acid and fatty acid esters of vitamin C for treatment of skin damage; U.S. Pat. No. 6,191,121, describes the use of polyenoylphosphatidyl choline to treat skin damage; U.S. Pat. Nos. 5,965,618 and 5,709,868, describe the treatment of scar tissue using lipoic acid, and additionally, alpha-hydroxy acids, fatty acid esters of vitamin C, and tocotrienol (vitamin E); and U.S. Pat. Nos. 5,554,647 and 5,643,586 describe the use of catecholamine or acetylcholine precursors for treatment of skin damage. Vitamins have been used to prevent or reverse skin damage, and in particular, skin damage associated with inflammation due to UV radiation. For example, U.S. Pat. Nos. 5,574,063, 5,545,398, 5,409,693, and 5,376,361 describe the use of fatty acid esters of ascorbic acid (e.g., vitamin C palmitate) or tocotrienol (vitamin E) for treatment and prevention of skin damage.

Skin creams may comprise several ingredients, some of which are beneficial to the skin, and others that promote absorption of active ingredients into the skin. For example, U.S. Pat. No. 4,362,747 describes a cream pack formulation which comprises a mixture of the following components: (1) propylene glycol and polyoxyethylene; (2) monopalmitate and glyoxyldiureide; (3) alcohol, beeswax, sorbitan monopalmitate, and polyoxyethylene; (4) alcohol, dimethicone copolyol, glyceryl monosterarate/polyoxyethylene; and (5) stearate and zinc or titanium oxide. U.S. Pat. No. 5,391,373 describes a skin cream comprising sodium lactate, a micellar complex of plant extracts, vitamin B, and glycosphingolipids, a protein complex of serum proteins, animal proteins, and glycogen, a carbohydrate based complex of dextran, glycine and glucosamine, a long-chain fatty acid ester of retinol, a long-chain fatty acid ester of ascorbic acid and a short chain fatty acid ester of tocopherol.

Certain treatments are designed to target specific skin problems. U.S. Pat. Nos. 5,958,397, 5,922,331, 5,817,621, 5,658,580, 5,362,488, 5,322,685, 5,254,331, 4,760,096, 4,297,374, 4,268,526, 4,087,555, and 4,007,266 all describe the formulation of skin creams which address specific aspects related to skin care. For example, U.S. Pat. No. 5,817,621 describes a skin cream comprising a lipid ointment, vitamin A, a salicylic acid, D-camphor, a biogenic GABAergic substance, a dopaminergic substance, M-cholionolyics, pancreatin, ascorbic acid, pantothenic acid calcium salt, and vitamin D2 as a means to cause a high trophoprotective effect followed by a restoration of skin physiological functions Still, none of the skin creams developed thus far have been effective enough to be entirely embraced by those suffering from damaged skin or wanting to deter aging of the skin. Although there are some treatments that are known to remedy specific skin conditions, there is a need for a simple all-in-one cosmetic treatment that increases skin firmness to thereby reduce aging and damage to the skin.

SUMMARY OF THE INVENTION

The present invention relates to a skin cream which can be used by most individuals on a daily basis to improve the skin firmness and the quality of skin tone. The skin cream of the present invention comprises at least one anti-oxidant, an anti-inflammatory agent, an exfoliant, and an agent to protect against UV irradiation. In addition, the skin cream of the present invention may comprise oils, creams, and/or other compounds to promote adsorption of the active ingredients and to increase vibrancy of the skin tone. Thus, in one aspect, the skin cream of the present invention comprises: (a) an antioxidant; (b) an anti-inflammatory agent; (c) a membrane stabilizer; (d) an exfoliation promoting compound; and (e) an agent to protect against UV irradiation, wherein (a), (b), (c), (d), and (e) are in amounts such that the application of the cream to the skin of an individual increases the thickness of collagen bundles in the individual's skin.

In another aspect, the skin cream of the present invention comprises: (a) dimethylaminoethanol (DMAE), (b) α-lipoic acid, (c) lactic acid, (d) retinol, (e) zinc oxide and/or titanium oxide (TiO, $TiO_2$, $TiO_3$, $Ti_2O_3$, $Ti_3O_5$), and (f) vitamin C, wherein components (a), (b), (c), (d), (e) and (f) are in amounts such that application of the cream to an individual increases the thickness of collagen bundles in the individual's skin. In various embodiments, the skin cream of the present invention also includes a vehicle or moisturizer base comprising at least one of xantham gum, carageenan, allantoin, vegetable glycerin, galactoarabinin, beeswax, emulsifying wax, Hi oleic sunflower oil, octyl stearate, squalane, dimethicone, shea butter, myristyl lactate, peg-7 glyceryl cocoate, dimethicone/octyldimethicone/ethoxyglucoside, methylparaben/propylparaben/ethylparaben/butylparaben in phenoxyethanol, or a fragrance.

The present invention also comprises methods for treating skin comprising application of the skin cream of the invention to increase firmness and tensile strength of the skin and reduce the onset of wrinkles. Thus, in another aspect, the present invention comprises a method for treating skin in an individual comprising application of a skin cream comprising: (a) an antioxidant; (b) an anti-inflammatory agent; (c) a membrane stabilizer; (d) an exfoliation promoting compound; and (e) an agent to reduce exposure of the skin to UV light, wherein (a), (b), (c), (d), and (e) are in amounts such that the application of the cream to the skin of an individual increases the thickness of collagen bundles in the individual's skin.

The foregoing focuses on the more important features of the invention in order that the detailed description which follows may be better understood and in order that the present contribution to the art may be better appreciated. There are, of course, additional features of the invention which will be described hereinafter and which will form the subject matter of the claims appended hereto. It is to be understood that the invention is not limited in its application to the specific details as set forth in the following description. The invention is capable of other embodiments and of being practiced or carried out in various ways.

From the foregoing summary, it is apparent that an object of the present invention is to provide methods and compositions for reducing damage and aging of the skin. These, together with other objects of the present invention, along with various features of novelty which characterize the invention, are pointed out with particularity in the claims and description provided herein.

DETAILED DESCRIPTION OF THE INVENTION

The present invention relates to a skin cream which will reduce wrinkling and increase the firmness and tensile strength of skin. The skin cream of the present invention employs several ingredients to increase the ability of skin to resist oxidative damage. In addition, the skin cream of the present invention employs components to reduce the effects of aging and to prevent further damage from occurring. In the description that follows, the singular forms "a", "an" and "the" include plural references unless the context clearly dictates otherwise.

Thus, in one aspect, the present invention comprises a skin cream comprising: (a) at least one antioxidant; (b) an anti-inflammatory agent; (c) a membrane stabilizer; (d) an exfoliation promoting compound; and (e) an agent to protect against UV irradiation, wherein (a), (b), (c), (d), and (e) are in amounts such that the application of the cream to the skin of an individual increases the thickness of collagen bundles in the individual's skin.

The present invention also comprises a method for treating skin comprising application of a skin cream to an individual, wherein the skin cream comprises: (a) at least one antioxidant; (b) an anti-inflammatory agent; (c) a membrane stabilizer; (d) an exfoliation promoting compound; and (e) an agent to protect against UV irradiation, wherein (a), (b), (c), (d), and (e) are in amounts such that the application of the cream to the skin of an individual increases the thickness of collagen bundles in the individual's skin.

The following embodiments may be understood to apply to both the cream and its' method of use. Preferably, the antioxidant comprises at least one of α-lipoic acid, vitamin C, dimethylaminoethanol (DMAE), an alpha- or beta-hydroxy acid, or vitamin A (retinol). Also preferably, the anti-inflammatory agent comprises α-lipoic acid and/or vitamin C. Also preferably, the membrane stabilizer comprises dimethylaminoethanol (DMAE). Also preferably, the compound that promotes exfoliation comprises an alpha- or beta-hydroxyacid. Even more preferably, the alpha-hydroxy acid is lactic acid. Also preferably, the compound to reduce exposure of the skin to UV light comprises zinc oxide and/or titanium oxide (TiO, $TiO_2$, $TiO_3$, $Ti_2O_3$, $Ti_3O_5$).

In an embodiment, the present invention comprises a skin cream that comprises a mixture of dimethylaminoethanol (DMAE), α-lipoic acid, lactic acid, retinol, zinc oxide and/or titanium oxide (TiO, $TiO_2$, $TiO_3$, $Ti_2O_3$, $Ti_3O_5$), and vitamin C. The DMAE in the cream may range from 0.1 to 5%, and more preferably is 1%. Also preferably, the concentration of α-lipoic acid ranges from 0.02 to 10%. More preferably, the concentration of α-lipoic acid is 0.2%. Also preferably, the concentration of lactic acid ranges from 2 to 20%. More preferably, the concentration of lactic acid is 10%. In yet another preferred embodiment, the amount of retinol in the cream of the present invention comprises 1,000 to 20,000 I.U. retinol per gram of cream. More preferably, the cream comprises about 10,000 I.U. retinol per gram of cream. The concentration of zinc oxide or titanium oxide (TiO, $TiO_2$, $TiO_3$, $Ti_2O_3$, $Ti_3O_5$) in the cream may range from 1 to 20%, and most preferably, is 9%. In a preferred embodiment, the concentration of vitamin C ranges from 0.5 to 20%. More preferably, the vitamin C concentration is 6%. Also preferably, the vitamin C is present as the phosphate of vitamin C.

The skin cream may also comprise additional ingredients, singly or in combination. Also, it is contemplated that compounds that are known to be similar in structure or chemical effect may be used in place of the specific components described herein. As only one example, natural oils other than sunflower oil may be employed, and waxes other that beeswax may be used as additional components in the cream of the present invention.

In an embodiment, the skin cream is water-based and thus, comprises deionized water. The skin cream may also comprise a thickening agent. In an embodiment the thickening agent is Xantham gum. Xantham gum is a thickening agent or emulsifier which is made from polysaccharides. Preferably, the concentration of Xantham gum ranges from 0.1 to 2%.

The skin cream may also comprise a natural polysaccharide. In an embodiment, the natural polysaccharide comprises Carrageenan. Carrageenan is a linear sulfated food grade polysaccharide obtained from red seaweed. Carrageenan, a powder when pure, may be formulated as a gel at room temperature to have a consistency ranging from smooth to almost rigid depending on the mix. Preferably, the concentration of Carrageenan ranges from 0.1 to 3%.

The skin cream may further comprise a compound to promote growth and repair of the skin. In an embodiment, the compound that promotes growth and repair of the skin comprises allantoin. Allantoin is a crystallizable substance that is found, for example, in plants, allantoic fluid, amniotic fluid, and fetal urine. Allantoin is used in medicine to promote repair in wounds and ulcers. Preferably, the concentration of allantoin ranges from 0.1 to 1%.

The skin cream may also comprise a normal moisturizing factor (nmf). In an embodiment, the normal moisturizing factor is vegetable glycerin, or the like. Vegetable glycerin, and/or other types of glycerins, are used in natural soaps to provide a normal moisturizing factor (nmf) lubricant. Preferably, the concentration of vegetable glycerin ranges from 1 to 10%.

The skin cream may also comprise additional compounds that promote exfoliation of the skin. In an embodiment, the compound that promotes exfoliation comprises galactoarabinan. Galactoarabinan promotes exfoliation without the irritation associated with alpha-hydroxy acids (AHAs) and thus, comprises an AHA booster. Preferably, the concentration of galactoarabinan ranges from 0.2 to 8%.

The skin cream may also comprise an emollient. Emollients act to soften or smooth the skin. In an embodiment, the emollient comprises myristyl lactate. Myristyl lactate comprises an emollient and emulsifier. Preferably, the concentration of the myristyl lactate ranges from 0.2 to 5%.

The skin cream may also comprise peg-7 glyceryl cocoate. Peg-7 glyceryl cocoate comprises an emollient and lipid layer enhancer. Preferably, the concentration of peg-7 glyceryl cocoate ranges from 0.1 to 5%.

The skin cream may also comprise a compound to help solubilize the various components of the cream. In an embodiment, the solubilization factor comprises beeswax, or the like. Beeswax is a complex mixture of organic compounds and acts as an emulsifying agent to help solubilize of the various components in the cream. An emulsifying agent is an ingredient which facilitates the blending of oil and water. The skin cream may also include an additional emulsifying waxes. Preferably, the concentration of beeswax ranges from 0.1 to 15%. Preferably, the concentration of the second emulsifying wax ranges from 0.1 to 15%.

The skin cream may also comprise an organic fatty acid. In an embodiment, the organic fatty acid comprises octyl stearate. Additionally, or alternatively, other long-chain fatty acids may be used. Octyl stearate may be used to create oil in water emulsions and also functions as a moisturizer, emollient, skin conditioner, and lubricant. Preferably, the concentration of octyl stearate ranges from 0.1 to 10%.

The skin cream may also include at least one natural oil. In an embodiment, the at least one natural oil comprises Hi oleic sunflower oil, or the like. For example, sunflower oil is a natural triglyceride with oxidative stability and emollient properties. Preferably, the concentration of sunflower oil ranges from 0.1 to 30%.

The skin cream may also comprise shea butter, or the like. Shea butter is a fatty substance obtained from the kernels of nuts of the shea tree. Preferably, the concentration of shea butter ranges from 0.1 to 20%.

The skin cream may also include squalane. Squalane is a saturated hydrocarbon also known as perhydrosqualene, and is obtained by hydrogenation of squalene, an aliphatic triterpene isolated from shark liver oil and olives. Squalane provides a natural oil which is compatible with cosmetic formulations. Preferably, the concentration of squalane ranges from 0.1 to 15%.

The skin cream may also comprise dimethicone, and derivatives thereof. Dimethicone is an oil derived from silcone. Dimethicone can increase the crosslinking of mucopolysaccharides, such as hyaluronic acid, to protein in connective tissue. Preferably, the concentration of dimethicone and/or derivatives thereof, ranges from 0.1 to 5%.

The skin cream may also comprise dimethicone/octyldimethicone/ethoxy-glucoside to give the cream a smooth silky feel. Thus, the dimethicone/octyl-dimethicone/ethoxy glucoside may be added to promote lubricity and as an SPF boost. In addition, the mixture comprises an emulsifier and dispersant for zinc oxide or titanium oxide ($TiO$, $TiO_2$, $TiO_3$, $Ti_2O_3$, $Ti_3O_5$), an emollient and film former. Preferably, the concentration of the mixture ranges from 0.1 to 5% for each component.

The skin cream may also comprise at least one preservative. In an embodiment, the preservative is a paraben and more preferably a mixture of parabens. Parabens comprise compounds which are derived from benzoic acid and are commonly used as preservatives in pharmaceuticals and cosmetics. In an embodiment, the paraben mixture comprises methylparaben/propylparaben/ethylparaben/butylparaben in phenoxyethanol. Also, the skin cream may comprise a fragrance to make application more pleasing.

Thus, the skin cream of the present invention may comprise a vehicle or moisturizer base in addition to the active ingredients. In an embodiment, the vehicle or moisturizer base comprises at least one of deionized water, xantham gum, carageenan, allantoin, vegetable glycerin, galactoarabinan, beeswax, emulsifying wax, Hi oleic sunflower oil; octyl stearate, squalane, dimethicone, shea butter, myristyl lactate, peg-7 glyceryl cocoate, dimethicone/octyldimethicone/ethoxyglucoside, zinc oxide and/or titanium oxide ($TiO$, $TiO_2$, $TiO_3$, $Ti_2O_3$, $Ti_3O_5$), methylparaben/propylparaben/ethylparaben/butylparaben in phenoxyethanol, or a fragrance.

The skin cream of the present invention promotes an increase in the tensile strength and firmness of the skin. Upon application, the cream of the present invention may reduce wrinkles. Also, application of the cream of the present invention leads to an overall increase in the thickness of the collagen bundles in the dermis. The increase in collagen bundle thickness is associated with increased firmness of the skin which in turn, generates a more youthful appearance.

Thus, preferably, application of the cream results in an increase of at least 10% in the thickness of collagen bundles in the dermis. More preferably, application of the cream results in an increase of at least 20% in the thickness of collagen bundles in the dermis. Even more preferably, application of the cream results in an increase of at least 50% in the thickness of collagen bundles in the dermis. Even more preferably, application of the cream results in an increase of at least 100% in the thickness of collagen bundles in the dermis.

The cream of the present invention may be applied as a regular part of skin care. In an embodiment, the cream of the present invention is applied 1 to 2 times a day. Preferably, noticeable results are seen within 3 months of regular (daily) application of the cream. More preferably, noticeable results are seen within 6 weeks, and more preferably, within 2 weeks of regular (daily) application of the cream.

In another aspect, the present invention comprises a skin cream comprising: (a) dimethylaminoethanol; (b) α-lipoic acid; (c) lactic acid; (d) retinol; (e) zinc oxide and/or titanium oxide ($TiO$, $TiO_2$, $TiO_3$, $Ti_2O_3$, $Ti_3O_5$); and (f) vitamin C, wherein components (a), (b), (c), (d), (e), and (f) are in amounts such that application of said cream to an individual increases the thickness of collagen bundles in the individual's skin.

Preferably, the skin cream comprises 0.1-5% dimethylaminoethanol, 0.02-10% α-lipoic acid, 2-20% lactic acid, 1,000-20,000 I.U. retinol/gram of cream, approximately 1-20% zinc oxide and/or titanium oxide ($TiO$, $TiO_2$, $TiO_3$, $Ti_2O_3$, $Ti_3O_5$), and approximately 0.5-20% vitamin C. More preferably, the skin cream comprises approximately 1% dimethylaminoethanol, approximately 0.2% α-lipoic acid, approximately 10% lactic acid, approximately 10,000 I.U. retinol/gram of cream, approximately 9% zinc oxide and/or titanium oxide ($TiO$, $TiO_2$, $TiO_3$, $Ti_2O_3$, $Ti_3O_5$), and approximately 6% vitamin C.

Also preferably, the skin cream comprises a vehicle or a moisturizer base. More preferably, the vehicle or a moisturizer base comprises at least one of deionized water, xantham gum, carageenan, allantoin, vegetable glycerin, galactoarabinan, beeswax, emulsifying wax, Hi oleic sunflower oil, octyl stearate, squalane, dimethicone, shea butter, myristyl lactate, peg-7 glyceryl cocoate, dimethicone/octyldimethicone/ethoxyglucoside, zinc oxide and/or titanium oxide (TiO, TiO$_2$, TiO$_3$, Ti$_2$O$_3$, Ti$_3$O$_5$), methylparaben/propylparaben/ethylparaben/butylparaben in phenoxyethanol, or a fragrance.

The present invention also comprises a method for treating skin comprising application of the skin cream of the invention. Thus, in another aspect, the present invention comprises a method for treating skin in an individual comprising application of a skin cream comprising: (a) an antioxidant; (b) an anti-inflammatory agent; (c) a membrane stabilizer; (d) an exfoliation promoting compound; and (e) an agent to reduce exposure of the skin to UV light, wherein (a), (b), (c), (d), and (e) are in amounts such that the application of the cream to the skin of an individual increases the thickness of collagen bundles in the individual's skin.

In a preferred embodiment, the skin cream comprises a mixture of dimethylaminoethanol (DMAE), α-lipoic acid, lactic acid, retinol, zinc oxide and/or titanium oxide (TiO, TiO$_2$, TiO$_3$, Ti$_2$O$_3$, Ti$_3$O$_5$), and vitamin C. Preferably, the skin cream comprises 0.1-5% dimethylaminoethanol, 0.02-10% α-lipoic acid, 2-20% lactic acid, 1,000-20,000 I.U. retinol/gram of cream, approximately 1-20% zinc oxide and/or titanium oxide, and approximately 0.5-20% vitamin C. More preferably, the skin cream comprises approximately 1% dimethylaminoethanol, approximately 0.2% α-lipoic acid, approximately 10% lactic acid, approximately 10,000 I.U. retinol per gram cream, approximately 9% zinc oxide or titanium oxide, and approximately 6% vitamin C.

The skin cream used to treat aging skin may also include a vehicle or a moisturizing base. Preferably, the vehicle or a moisturizing base comprises at least one of deionized water, xantham gum, carageenan, allantoin, vegetable glycerin, galactonarabinan, beeswax, emulsifying wax, Hi oleic sunflower oil, octyl stearate, squalane, dimethicone, shea butter, myristyl lactate, peg-7 glyceryl cocoate, dimethicone/octyldimethicone/ethoxyglucoside, zinc oxide and/or titanium oxide (TiO, TiO$_2$, TiO$_3$, Ti$_2$O$_3$, Ti$_3$O$_5$), methylparaben/propylparaben/ethylparaben/butylparaben in phenoxyethanol, or a fragrance.

Upon application, the skin cream of the present invention promotes an increase in firmness and tensile strength of the skin and may reduce wrinkles. Also, application of the cream of the present invention leads to an overall increase in the diameter of collagen bundles. The increase in collagen bundle diameter is associated with increased firmness of the skin, to generate a more youthful appearance.

Thus, preferably, application of the cream results in an increase of at least 10% in the thickness of collagen bundles in the dermis. More preferably, application of the cream results in an increase of at least 20% in the thickness of collagen bundles in the dermis. Even more preferably, application of the cream results in an increase of at least 50% in the thickness of collagen bundles in the dermis. Even more preferably, application of the cream results in an increase of at least 100% in the thickness of collagen bundles in the dermis.

The cream of the present invention may be applied as a regular part of skin care. Thus, in an embodiment, the cream of the present invention is applied 1 to 2 times a day. Also in an embodiment, noticeable results are seen within 3 months of regular (daily) application of the cream. More preferably, noticeable results are seen within 6 weeks, and more preferably, within 2 weeks of regular (daily) application of the cream.

The skin cream of the present invention targets several aspects of skin aging. The skin cream of the present invention includes antioxidants to reduce damage due to free radicals. Free radicals are generated upon exposure of skin to sunlight and toxins, such as chemicals, air pollution, and cigarette smoke. Free radicals comprise chemical species which are chemically unstable in that they contain an unpaired electrons and thus, can activate cellular molecules to become chemically reactive, often with detrimental results. Free radicals have the ability to damage cellular DNA and protein, including the membranes of skin cells. In addition to direct chemical interaction with cellular components, free radicals can cause inflammation of the tissue. Thus, free-radicals increase production of arachidonic acid and other pro-inflammatory molecules.

To reduce damage done by free radicals, the cream of the present invention contains at least one anti-oxidant. Antioxidants prevent free radical damage by giving the highly reactive free radicals electron partners, without becoming reactive themselves.

In an embodiment, the cream of the present invention comprises the anti-oxidant α-lipoic acid. As an anti-oxidant, α-lipoic acid is highly effective because it is both water and fat soluble, and therefore, is effective both inside the cell, and in the cell membrane.

In addition to its anti-oxidant function, α-lipoic acid may act as an anti-inflammatory agent. For example, α-lipoic acid prevents the activation of transcription factors, such as NFκ-B, and thereby prevents the cell from producing pro-inflammatory cytokines that are induced by NFκ-B. Also, α-lipoic acid may activate the transcription factor AP-1 to induce production of enzymes which degrade damaged collagen, thereby removing damaged skin (see e.g., Perricone, N., *The Wrinkle Cure*, Warner Books, New York, N.Y., 2000, at p. 72). Finally, α-lipoic acid can prevent collagen and other proteins from becoming cross-linked to each other, due to the addition of sugar residues (glycation). Thus, α-lipoic acid can help preserve the amount of functional collagen in skin cells.

In an embodiment, the cream of the present invention comprises vitamin C. Vitamin C also may act as both an anti-oxidant and an anti-inflammatory agent. For example, vitamin C may act as an anti-inflammatory agent by reducing the formation of arachidonic acid. In addition, vitamin C facilitates collagen synthesis. In a preferred embodiment, the vitamin C is ascorbyl phosphate, although fatty acid esters of vitamin C, such as vitamin C oleate and palmitate, may be used.

The skin cream of the present invention also comprises dimethylaminoethanol (DMAE). DMAE and other alkanolamines act as anti-oxidants and membrane stabilizers. Thus, in an embodiment, DMAE intersperses in the membrane and prevents the action of oxidants in the membrane. In addition, DMAE may act on nerves in the dermis to increase the effectiveness of the neurotransmitters such as acetylcholine and catecholamines (U.S. Pat. No. 6,191,121; Perricone, 2000, pp 81-85).

The skin cream of the present invention can reverse and/or reduce the onset of wrinkles and other skin changes typical of aging by increasing the elasticity of the skin and improving skin tone. Compounds that can aid in wrinkle reduction are exfoliation promoting agents. These compounds promote the loss of the skin's upper layer (usually dead cells) thus allowing for younger, smoother tissue to be at the skin's surface. Thus, the skin cream of the present invention comprises lactic acid as an exfolliant. Lactic acid is an a-hydroxy acid derived from milk. Alpha and beta hydroxyacids may promote exfoliation of the upper layer of the epidermis, thereby improving the smoothness of skin. In addition, alpha and beta hydroxy acids act as anti-oxidants, and thereby reduce and reverse free radical damage and may stimulate collagen production.

The skin cream of the present invention also comprises retinol. Retinol is a form of vitamin A. Vitamin A acts as an anti-oxidant thereby reducing damage due to free radicals. Vitamin A acts on protein synthesis and cell membrane structure. Specifically, vitamin A improves epidermal cell regeneration, stimulates collagen synthesis, and reduces the production of matrix metalloproteinases involved in collagen damage. A deficiency in vitamin A leads to an alteration of the skin organization, dryness, and hyperkeratosis.

The skin cream of the present invention also comprises a UV radiation blocker to reduce UV damage to the skin. UV light is detrimental in that it increases breakdown of cells in the epidermis and dermis to increase wrinkling. In addition, excess sun exposure may have serious health effects such as the development of melanoma and other types of skin cancer.

EXAMPLES

The present invention may be better understood by reference to the following non-limiting examples.

Example 1

Formulation of a Skin Cream of the Present Invention

A skin cream was made having the components shown in Table 1.

TABLE 1

Skin Cream

| Ingredient | Treatment cream (Tx) | Vehicle (Ve) |
|---|---|---|
| DMAE | 1.0% | — |
| Lipoic Acid | 0.2% | — |
| Lactic Acid | 10.0% | — |
| Retinol | 10,000 IU/gram | — |
| Zinc oxide or titanium oxide (TiO, $TiO_2$, $TiO_3$, $Ti_2O_3$, $Ti_3O_5$) | 9.0% | — |
| Vitamin C | 6.0% | — |
| Xantham Gum | 0.1-2% | 0.1-2% |
| Carrageenan | 0.1-3% | 0.1-3% |
| Allantoin | 0.1-1% | 0.1-1% |
| Vegetable glycerin | 1-10% | 1-10% |
| Galactoarabinan | 0.2-8% | 0.2-8% |
| Beeswax | 0.1-15% | 0.1-15% |
| Emulsifying wax | 0.1-15% | 0.1-15% |
| Hi oleic sunflower oil | 0.1-30% | 0.1-30% |
| Octyl stearate | 0.1-10% | 0.1-10% |
| Squalane | 0.1-15% | 0.1-15% |
| Dimethicone | 0.1-5% | 0.1-5% |
| Shea Butter | 0.1-20% | 0.1-20% |
| Myristyl Lactate | 0.2-5% | 0.2-5% |
| Peg-7 glyceryl cocoate | 0.1-5% | 0.1-5% |
| Dimethicone/octyldimethicone/ethoxyglucoside | 0.1-5% | 0.1-5% |
| Zinc oxide or titanium oxide (TiO, $TiO_2$, $TiO_3$, $Ti_2O_3$, $Ti_3O_5$) | 2% | 2% |
| Methylparaben/propylparaben/ethylparaben/butylparaben in phenoxyethanol | 0.8% | 0.8% |
| Fragrance | <5% | <5% |
| Sodium Citrate Buffer (pH 7.0) | 0.5%-1.0% | 0.5%-1.0% |
| Deionized water | to 100% | to 100% |

Example 2

Double-Blind Study

A skin cream of the present invention was used in a double-blind study to test the effectiveness of the cream in improving skin texture. The study population consisted of 8 patients, male and female, who ranged in age from 30+ to 70+ as delineated in Table 2. The youngest female patient dropped out of the study after the first biopsy.

TABLE 2

Patients in Double-Blind Study

| Age | 30+ | 40+ | 50+ | 60+ | 70+ |
|---|---|---|---|---|---|
| Male | 1 | 1 | 0 | 1 | 0 |
| Female | 1 | 1 | 1 | 1 | 1 |

The study employed the cream shown in Table 1 as the treatment cream (Tx). As a control, a vehicle cream (Ve) without the active ingredients (DMAE, lipoic acid, lactic acid, retinol, high levels (>2%) of titanium oxide (TiO, $TiO_2$, $TiO_3$, $Ti_2O_3$, $Ti_3O_5$), and/or zinc oxide, and vitamin C) was used. The vehicle cream is essentially a moisturizer.

Punch biopsy samples (3 mm) were taken from one hand of each patient before and after treatment with either the test cream or the vehicle cream described in Table 1. Pre-treatment (first) biopsies were taken 1.5 cm from the webspace of the $4^{th}$ and $5^{th}$ fingers on the dorsal hand surface. Post-treatment (second) biopsies were performed 0.5 cm from the original site.

Individuals were instructed to apply a fingertip unit of either the test cream or the vehicle cream to the dorsal surface of one hand twice a day, and also to the region of the face near the eyes where "crows feet" wrinkles can be found. The test cream (Tx) was used on either the left (L) or right (R) hand and eye as indicated in Table 3 (with the vehicle applied to the other hand and eye as a control). The study was performed in a "double blind" manner, wherein neither the subject nor the investigator performing the measurements knew which side (i.e. left or right) had the test cream (Tx) applied and which side had the vehicle (Ve) applied.

Samples from the hand were evaluated by measuring the thickness of either the stratum corneum (Sc), epidermis (including the stratum corneum) (Ep), and collagen bundles in the upper layer of the dermis (Cb) using an ocular micrometer using standard methods. For each of these three measurements (Sc, Ep and Cb), approximately 20 to 30 measurements were taken for each 3 mm biopsy, and the values averaged. All reported measurements are in microns. In addition, the skin near the eyes and on the hands was inspected visually, grading wrinkling on a scale of 1-10, with 10 being the most wrinkling. Results are shown in Table 3.

TABLE 3

Measurement of Wrinkling and Elastin Fiber Diameter on Subjects in Study

| Subject | Tx | Ve | Pre R Hand | Post R Hand | Pre L Hand | Post L Hand | Pre R Eye | Post R Eye | Pre L Eye | Post L Eye | Biop Pre R | Biop Post R | Biop Pre L | Biop Post L |
|---|---|---|---|---|---|---|---|---|---|---|---|---|---|---|
| 1 | L | R | 3 | 3 | 3 | 4.5 | 4 | 3 | 4 | 4.5 | Sc = 30<br>Ep = 110<br>Cb = 10 | Sc = 22.5<br>Ep = 100<br>Cb = 10 | Sc = 40<br>Ep = 150<br>Cb = 10 | Sc = 30<br>Ep = 100<br>Cb = 20 |
| 2 | L | R | 4 | 3 | 4 | 4.5 | 4 | 3 | 4 | 4.5 | Sc = 100<br>Ep = 210<br>Cb = 10 | Sc = 40<br>Ep = 200<br>Cb = 12 | Sc = 50<br>Ep = 200<br>Cb = 10 | Sc = 80<br>Ep = 140<br>Cb = 15 |
| 3 | R | L | 4 | 4 | 4 | 3 | 5 | 4 | 4 | 3 | Sc = 80<br>Ep = 180<br>Cb = 10 | Sc = 50<br>Ep = 125<br>Cb = 15 | Sc = 50<br>Ep = 175<br>Cb = 10 | Sc = 75<br>Ep = 150<br>Cb = 10 |
| 4 | R | L | 6 | 6 | 5 | 4 | 6 | 6 | 7 | 5 | Sc = 30<br>Ep = 100<br>Cb = 10 | Sc = 30<br>Ep = 90<br>Cb = 12.5 | Sc = 40<br>Ep = 100<br>Cb = 10 | Sc = 30<br>Ep = 100<br>Cb = 10 |
| 5 | L | R | 6 |  | 6 |  | 6 |  | 7 |  | Sc = 50<br>Ep = 200<br>Cb = 10 | Sc = 40<br>Ep = 115<br>Cb = 10 | Sc = 100<br>Ep = 200<br>Cb = 10 | Sc = 50<br>Ep = 110<br>Cb = 15 |
| 6 | R | L | 8 | 7 | 7 | 6 | 8 | 7 | 7 | 6 | Sc = 50<br>Ep = 120<br>Cb = 10 | Sc = 20<br>Ep = 50<br>Cb = 15 | Sc = 75<br>Ep = 175<br>Cb = 10 | Sc = 30<br>Ep = 120<br>Cb = 10 |
| 7 | L | R | 7 |  | 7 |  | 7 |  | 8 |  | Sc = 50<br>Ep = 120<br>Cb = 10 | Sc = 50<br>Ep = 110<br>Cb = 15 | Sc = 50<br>Ep = 100<br>Cb = 10 | Sc = 40<br>Ep = 80<br>Cb = 10 |

Sc: stratum corneum; Ep: epidermis (including stratum corneum); Cb: collagen bundles in upper layer of dermis. Biopsy results are the average values for n = 20-30 measurements per 3 mm biopsy; values are in microns.

It was found that there was a general improvement in wrinkling over the course of the study for subjects 3, 4 and 6 for both the treatment cream and the vehicle moisturizer. It was found, however, that there was a significant increase in the diameter of collagen bundles in the upper layer of the dermis for the hand treated with the test cream (as compared to the vehicle). Thus, for subjects 1, 2, 3, 4, 5, and 6 there was a 20% to 100% increase in the collagen bundles of the treated hand, with little to no increase in the control hand.

It will be understood that each of the elements described above, or two or more together, may also find utility in applications differing from the types described herein. While the invention has been illustrated and described as a method for increasing elasticity in the skin, it is not intended to be limited to the details shown, since various modifications and substitutions can be made without departing in any way from the spirit of the present invention. For example, emulsifiers and adsorption promoting agents other than those described may be employed. As such, further modifications and equivalents of the invention herein disclosed may occur to persons skilled in the art using no more than routine experimentation, and all such modifications and equivalents are believed to be within the spirit and scope of the invention as defined by the following claims. All references cited herein are incorporated by reference in their entirety.

What is claimed is:

1. A skin cream comprising: (a) about 0.1-5% dimethylaminoethanol; (b) about 0.02-10% α-lipoic acid; (c) about 2-20% lactic acid; (d) about 1,000-20,000 I.U. retinol; (e) about 9% of at least one of zinc oxide or titanium oxide; and (f) about 6% ascorbyl phosphate as the only source of vitamin C, and a vehicle or moisturizer base, such that application of the cream to the skin of an individual increases the thickness of collagen bundles in the individual's skin.

2. The skin cream of claim 1, comprising approximately 1% dimethylaminoethanol, approximately 0.2% α-lipoic acid, approximately 10% lactic acid, approximately 10,000 I.U. retinol per gram cream, approximately 9% of at least one of zinc oxide or titanium oxide, and approximately 6% ascorbyl phosphate.

3. The skin cream of claim 1, wherein the vehicle or moisturizer base comprises octyl stearate, and xantham gum.

4. The skin cream of claim 3, wherein the vehicle or moisturizer base further comprises at least one of deionized water, carageenan, allantoin, vegetable glycerin, galactoarabinan, beeswax, emulsifying wax, Hi-oleic sunflower oil, squalane, dimethicone, shea butter, myristyl lactate, peg-7 glyceryl cocoate, dimethicone/octyldimethicone/ethoxyglucoside, methylparaben/propylparaben/ethylparaben/butylparaben in phenoxyethanol, or a fragrance.

5. A method for treating skin to increase the thickness of collagen bundles in an individual's skin comprising application of the skin cream of claim 1.

6. The method of claim 5, wherein the skin cream comprises approximately 1% dimethylaminoethanol, approximately 0.2% α-lipoic acid, approximately 10% lactic acid, approximately 10,000 I.U. retinol per gram of cream, approximately 9% zinc oxide and/or titanium oxide, and approximately 6% ascorbyl phosphate.

7. The method of claim 5, wherein the vehicle or moisturizer base comprises water, a silicone-based oil, a thickening agent, a polysaccharide, a compound to promote skin growth and repair, a moisturizing factor, an emollient, an organic fatty acid, and at least one of a natural fat or oil.

8. The method of claim 5, wherein the vehicle or moisturizer base comprises at least one of deionized water, octyl stearate, xantham gum, carageenan, allantoin, vegetable glycerin, galactoarabinan, beeswax, emulsifying wax, Hi-oleic sunflower oil, squalane, dimethicone, shea butter, myristyl lactate, peg-7 glyceryl cocoate, dimethicone/octyldimethicone/ethoxyglucoside, methylparaben/propylparaben/ethylparaben/butylparaben in phenoxyethanol, or a fragrance.

9. The method of claim 5, wherein application of the cream results in an increase of 10-100% in the thickness of collagen bundles in the dermis.

10. The method of claim 5, wherein application of the cream results in an increase of 20% in the thickness of the collagen bundles in the dermis.

11. The method of claim 5, wherein application of the cream results in an increase of 50% in the thickness of collagen bundles in the dermis.

12. The method of claim 5, wherein application of the cream results in an increase of 100% in the thickness of collagen bundles in the dermis.

13. The method of claim 5, where the cream is applied once or twice daily for at least 2 weeks.

14. The method of claim 5, where the cream is applied once or twice daily for at least 6 weeks.

15. The method of claim 5, where the cream is applied once or twice daily for at least 3 months.

16. The skin cream of claim 1, wherein the vehicle or moisturizer base comprises water, a silicone-based oil, a thickening agent, a polysaccharide, a compound to promote skin growth and repair, a moisturizing factor, an emollient, an organic fatty acid, and at least one of a natural fat or oil.

17. A skin cream comprising approximately 5% dimethylaminoethanol, approximately 5% α-lipoic acid, approximately 5% lactic acid, approximately 10,000 I.U. retinol per gram cream, approximately 6.5% of at least one of zinc oxide or titanium oxide, and approximately 3% ascorbyl phosphate and a vehicle or moisturizer base, such that application of the cream to the skin of an individual increases the thickness of collagen bundles in the individual's skin.

18. A method for treating skin in an individual comprising application of a skin cream comprising approximately 5% dimethylaminoethanol, approximately 5% α-lipoic acid, approximately 5% lactic acid, approximately 10,000 I.U. retinol per gram of cream, approximately 6.5% of at least one of zinc oxide or titanium oxide, and approximately 3% ascorbyl phosphate and a vehicle or moisturizer base, such that application of the cream to the skin of an individual increases the thickness of collagen bundles in the individual's skin.

19. A skin cream consisting essentially of: (a) about 5% dimethylaminoethanol; (b) about 5% α-lipoic acid; (c) about 5% lactic acid; (d) about 10,000 I.U. retinol per gram of cream; (e) about 6.5% of at least one of zinc oxide or titanium oxide; and (f) about 3% ascorbyl phosphate as the only vitamin C source; and a vehicle or moisturizer base having water, a silicone-based oil, a thickening agent, a polysaccharide, a compound to promote skin growth and repair, a moisturizing factor, an exfollient, an emollient, a wax, an organic fatty acid, and at least one of a natural fat or oil.

* * * * *